(12) United States Patent
Johnson

(10) Patent No.: US 12,186,238 B2
(45) Date of Patent: Jan. 7, 2025

(54) MULTIPLE SHADE AUTO DARKENING LENS FOR WELDING HELMETS

(71) Applicant: Hunter Colby Johnson, Atlanta, GA (US)

(72) Inventor: Hunter Colby Johnson, Atlanta, GA (US)

( * ) Notice: Subject to any disclaimer, the term of this patent is extended or adjusted under 35 U.S.C. 154(b) by 503 days.

(21) Appl. No.: 17/478,225

(22) Filed: Sep. 17, 2021

(65) Prior Publication Data

US 2022/0265473 A1     Aug. 25, 2022

Related U.S. Application Data

(60) Provisional application No. 63/207,283, filed on Feb. 22, 2021.

(51) Int. Cl.
*A61F 9/06* (2006.01)
*B23K 9/32* (2006.01)

(52) U.S. Cl.
CPC ............... *A61F 9/065* (2013.01); *B23K 9/32* (2013.01)

(58) Field of Classification Search
CPC . A61F 9/065; A61F 9/067; A61F 9/06; B23K 9/322; B23K 9/32
See application file for complete search history.

(56) References Cited

U.S. PATENT DOCUMENTS

| 5,140,707 | A | 8/1992 | Johnson |
| 5,959,705 | A | 9/1999 | Fergason |
| 2017/0252215 | A1* | 9/2017 | Wu ........................ A61F 9/065 |

OTHER PUBLICATIONS

FLIR Systems FAQ entitled "Can Thermal Imaging See Through Walls? And Othwer Common Questions" (as captured by Archive.org Oct. 20, 2019), 4 pages.
Amazon Listing for "Lincoln Electric 2×4 C-Series Auto-Darkening Welding Lens Variable Shade 8-13 KP3775-1" noting Date First Available: Jun. 27, 2019, 7 pages.
Lincoln Electric product literature entitled "2×4C Series—Auto Darkening Lenses with 4C® Lens Technology," issued by Lincoln Electric May 2018, 8 pages.
"Smartweld ADF Replacement Drop-In: SKU: 46411" on JacksonSafety.com, 2 pages.
Website of D5A capture by Archive.org showing availability Dec. 1, 2020, 2 pages.
Toll Gas product listing of "Miller 2×4-1/4" Shade 10 Auto-Darkening Welding Lens For Fixed Front and Lift Front Welding Helmets" (as captured by Archive.org on Nov. 28, 2020), 2 pages.

\* cited by examiner

*Primary Examiner* — Ryan D Howard
(74) *Attorney, Agent, or Firm* — Dowell & Dowell, P.C.

(57) ABSTRACT

A welding lens includes a variable light transmission shutter that automatically darkens in response to light emitted from a source. An intensity of the emitted light is sensed by a photo-sensor located on a front face of the welding lens. Internal circuits located within a housing of the welding lens receive data from the photo-sensor and correspondingly darkens or lightens the variable light transmission shutter based on the intensity of the light. The housing is 50.80 mm in width and 107.95 mm in length to fit in corresponding welding helmets and the housing is made from stainless steel to reflect infrared radiation that would otherwise overheat the internal circuits within the welding lens.

19 Claims, 7 Drawing Sheets

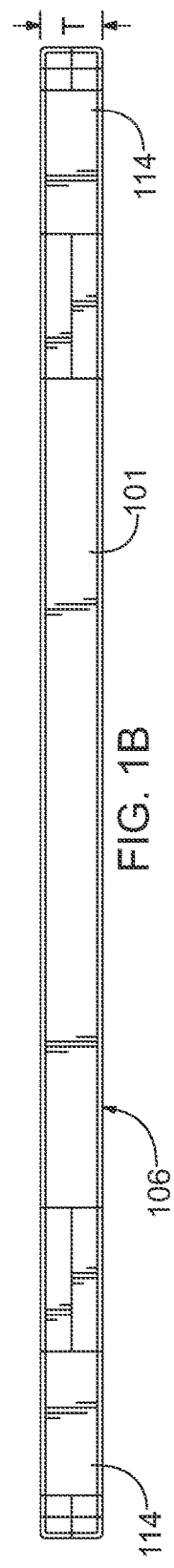
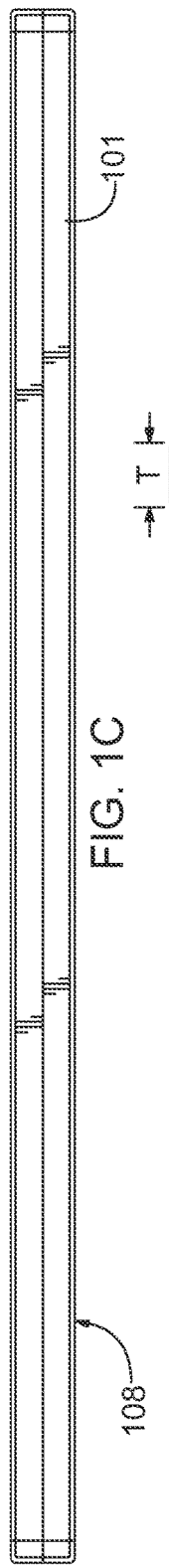
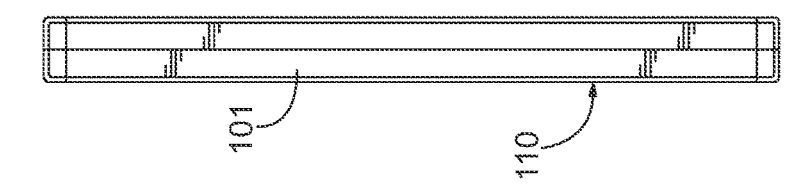

MULTIPLE SHADE AUTO DARKENING LENS FOR WELDING HELMETS

CROSS-REFERENCE TO RELATED APPLICATIONS

The present application claims priority to U.S. Provisional Application No. 63/207,283, filed on Feb. 22, 2021.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO A SEQUENCE LISTING

Not applicable.

STATEMENT REGARDING PRIOR DISCLOSURES BY THE INVENTOR OR A JOINT INVENTOR

Not applicable.

BACKGROUND OF THE INVENTION

Field of the Invention

The present invention relates generally to the field of welding. More specifically, the present invention relates to a visual-assistance device used during welding, typically referred to as a welding lens. The welding lens is provided on a welding helmet worn by a user performing welding activities for eye-safety purposes.

Brief Discussion of the Prior Art

The welding helmet is commonly worn during arc welding processes to prevent arc eye, which is an inflamed cornea. The welding helmet can also prevent loss of vision due to retina burns. Arc eye and retina burns are both caused by unprotected exposure to highly concentrated ultraviolet and infrared rays emitted by the welding arc. Ultraviolet emissions from the welding arc can also damage uncovered skin, causing a sunburn-like condition in a relatively short period of welding. In addition to radiation emissions, gases and splashes of super-heated liquid material can also injure a welder not wearing proper protection.

The first, traditional welding helmets included a window covered with a filter, called a lens shade, through which the welder could see to perform welding work. In most such welding helmets, the window may be made of tinted glass, tinted plastic, or a variable-density filter made from a pair of polarized lenses. Different lens shades have different degrees of shade, which are needed for different welding processes. For example, a lighter shade is preferred with metal inert gas (MIG) welding (also known as gas metal arc welding (GMAW)) and Tungsten inert gas (TIG) welding (also known as gas Tungsten arc welding (GTAW)).

The shade of the lens shade suitable for a particular welding process depends on the amperage rating of the weld. According to OSHA, welding work ranging from 50 to 60 amperes (A) requires a shade number of at least DIN 10. For a welding process dealing with arcs in the range 60 to 160 A, a DIN shade number of 11 is recommended. The DIN number, which is an internationally-accepted standard set by the Deutsches Institut für Normung (DIN), increases with an increase in amperage rating. The eyesight of the welder is also an essential factor for determining proper shading of a welding lens.

In 1981, a Swedish manufacturer, Hornell International, introduced a liquid crystal display (LCD) electronic light shutter that replaced the traditional lens shade. The LCD light shutter darkens automatically when photo-sensors detect the bright welding arc. With such an auto-darkening light shutter, the welder no longer has to get ready to weld and then nod their head to lower the helmet over their face, as the lens shade would inhibit normal eye sight in the absence of the light from the welding arc. Such welding helmets provide an advantage over the traditional welding helmet in that the welder does not need to adjust the position of welding helmet manually. This saves time and reduces the risk of exposure to harmful light generated by the welding process.

In an exemplary auto-darkening light shutter, or other systems in which it is desired automatically to control light transmission, a controllable light shutter is controlled to respective dark and/or bright or clear states and possibly to intermediate states there between. The light shutter may be, for example, an LCD shutter or some other light shutter that controls light transmission, for example, without affecting image characteristics of light transmitted through the light shutter. Operating circuitry connected to the light shutter operates the light shutter to assume the respective states, and a light sensor senses light conditions and provides an input to the operating circuitry to operate the shutter in response to the sensed light conditions. The photo-sensor provides an output representative of that light. The light may be in the visible, ultraviolet, infrared, or some other spectrum range or combination of ranges.

In an exemplary auto-darkening lens, the photo-sensor is placed at a front of a support structure or housing in which the light shutter is mounted, or the photo-sensor may be located within the support structure (e.g., the housing), which is provided with an access opening to allow light to reach the sensor. The location at which the sensor is mounted on or in the support structure may be selected to allow the light sensor to receive incident light that is representative of light which impinges on the shutter. It is desirable that the intensity of the light incident on the photo-sensor would be representative of the light incident on the shutter. In an auto-darkening light lens or other controllable light shutter device used for welding, it is desirable to detect light representing the occurrence of welding and to distinguish such light from ambient light.

Currently, auto-darkening light shutters made for welding applications that can perform on the full spectrum of welding amperages are larger than 2 inches (in.)×4.25 in., or 50.80 millimeters (mm)×107.95 mm. This is due to the size of internal electronic components and heat dissipation requirement for the internal electronic components at higher amperages. Current auto-light shutters cannot dissipate sufficient heat to prevent overheating internal electronic components at the 50.80 mm×107.95 mm size.

The field of art currently includes attempted solutions to this issue. There are larger-view welding helmets that have a lens with a large surface area and larger dimensions to help internal electronic components cool. However, these welding helmets offer several draw backs. One such limitation is a lack of focused viewing area. Further, the large surface area may let light from another welder's arc pass through the lens if welding occurs in cramped conditions. Many welders prefer a smaller lens. These welders using smaller auto-darkening lens must switch between lenses for different intensities if they weld in both high amperage and low amperage applications.

Currently, there is a need in the art for an auto-darkening welding lens that provides adequate darkening across a full spectrum of applicable amperages that also provides a small surface area window for viewing welding processes and adequate heat dissipation for preserving on-board internal electronic components.

SUMMARY OF THE INVENTION

The present invention addresses this need in the art by providing a welding lens, comprising a lens housing having a front face and a back face, the front face and back face being oppositely positioned; the front face having a photovoltaic cell, at least one photo-sensor, and a variable light transmission shutter; and the back face having a control panel and the variable light transmission shutter, wherein the lens housing is made of a metal that reflects infrared radiation and has a width of 50.80 millimeters (mm) and a length of 107.95 mm, and wherein the variable light transmission shutter automatically darkens to a dark state in response to the at least one photo-sensor receiving a high-intensity light and automatically reverts to a light state when the at least one photo-sensor does not receive the high-intensity light.

A further embodiment of the welding lens includes internal electronic components in electronic communication with the photovoltaic cell, the at least one photo-sensor, and the variable light transmission shutter.

The internal electronic components may provide an anti-light interference function that reduces flickering in the variable light transmission shutter by reducing sensitivity to ambient light fluctuations.

The internal electronic components may provide a gradual change delay function which delays time taken for the variable light transmission shutter to automatically revert to the light state from the dark state.

When the gradual change delay function is active, the variable light transmission shutter takes 0.5 seconds to revert from the light state to the dark state, and, when the gradual change delay function is inactive, the variable light transmission shutter takes 0.1 seconds to revert from the light state to the dark state.

The internal electronic components may provide a grind mode and a welding mode. The grind mode provides a shade value of 5 DIN. The welding mode provides a shade value of 8-13 DIN.

The welding lens may further include a shade button, a sensitivity button, and a delay button in electronic communication with the internal electronic components. The shade button toggles between different shade values and toggles between a grind mode and a welding mode, the grind mode providing a shade value of 5 DIN and the welding mode providing a shade value between 8-13 DIN. The sensitivity button toggles between different sensitivity values and activates and deactivates an anti-light interference function that reduces flickering in the variable light transmission shutter by reducing sensitivity to ambient light fluctuations. The delay button toggles between different delay values and activates and deactivates a gradual change delay function, which, when active, the variable light transmission shutter takes 0.5 seconds to revert from the light state to the dark state, and, when the gradual change delay function is inactive, the variable light transmission shutter takes 0.1 seconds to revert from the light state to the dark state.

The welding lens may further include at least one battery. The photovoltaic cell and the battery may both provide electric power to internal electronic components of the welding lens.

The welding lens may further include the lens housing with a thickness of 7.112 mm.

The stainless steel of the lens housing reflects infrared light, which reduces heat build-up in the welding lens.

The lens frame may include two removable panels, each panel of the two removable panels housing a battery of the at least one battery between each said panel and the lens frame.

The welding lens may further include a control panel having a display indicating a sensitivity value, a shade value, and a delay value. The control panel further comprises a sensitivity button to change the sensitivity value, a shade button to change the shade value, and a delay button to change the delay value.

The metal that reflects the infrared radiation may be stainless steel, copper, gold, silver, aluminum, or alloys thereof.

A welding helmet may include the welding lens embodiment, and any alternative embodiments, or combinations thereof.

BRIEF DESCRIPTION OF THE SEVERAL VIEWS OF THE DRAWINGS

A better understanding of the embodiments of the present invention will be had with reference to the following figure:

FIG. 1B is a view along a top surface of the welding lens of FIG. 1A;

FIG. 1C is a view along a bottom surface of the welding lens of FIG. 1A;

FIG. 1D is a view along a right side surface of the welding lens of FIG. 1A, the right side and a left side which are mirrors of each other;

FIG. 1E is a view along a left side surface of the welding lens of FIG. 1A;

DETAILED DESCRIPTION OF THE INVENTION

Figure 1A:
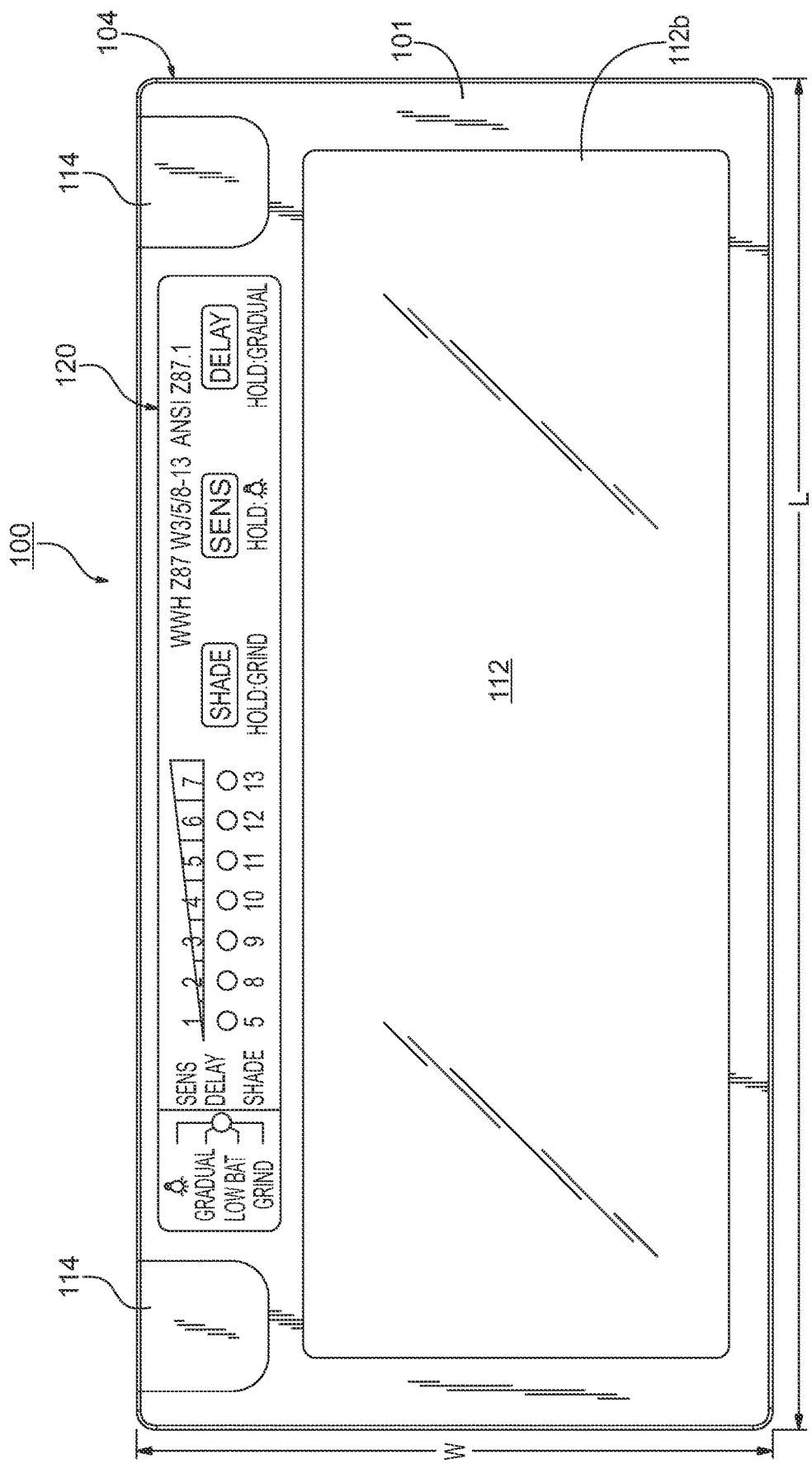
FIG. 1A is a view along a back face of a preferred embodiment of the welding lens of the present invention.

Reference will be made to a lens (also sometimes referred to as a "welding lens," "welding filter," "light shutter," and the like, and to an automatically darkening lens (sometimes referred to as auto-darkening lens)) that is able to operate automatically to control transmission of light. The lens may be a light shutter type of a device that is able to control light transmission without distorting, or at least with relatively minimal distortion, of the light and the image characteristics carried by the light or represented by the light. Therefore, when a person looks through the lens, the image seen would be substantially the same as the image seen without the lens, except that the intensity of the light transmitted through the lens may be altered depending on the operative state of the lens. The lens may be used in a welding helmet, and the lens may be used in other types of devices, such as goggles, spectacles, face masks, e.g., for industry (such as in an industrial plant or to protect outdoor or indoor electrical workers), respirator systems, nuclear flash eye protection devices, and other types of personal protective gear that serves to protect the wearer from light-based injury. Such devices usually are employed to protect the face or the eyes of a person, as is known, for example, in the field of welding. Further, the lenses may be used in various other places and for other purposes to protect workers from bright light that could present a risk of injury.

For the purposes of providing eye protection, usually a welding lens provides light blocking characteristics along the lens shade or light shutter in the visible, infrared, and/or ultraviolet wavelength ranges to protect a user's eyes. The actual ranges may be determined by the components of the lens, the arrangement of those components, and so forth.

The high-intensity light defined herein, and referred to as "arc rays," relates to electromagnetic radiation, or light, emitted from a welding arc generated during GMAW or GTAW. The exact intensity of light emitted from the welding arc varies between applications. However, the light emitted from all welding arcs is dangerous to unprotected eyes.

A preferred embodiment of an automatically darkening welding lens 100 is shown in FIGS. 1A-1F. The welding lens 100 includes a lens housing 101, which secures and contains constituent parts of the welding lens. The housing 101 preferably has at least two defined faces, a front face 102 and a back face 104. The front face 102 and the back 104 are oppositely oriented, or face opposite directions. The lens housing 101 preferably has a length L and a width W, with both the front face 102 and the back face 104 being defined by the length L and the width W of the housing along their respective surfaces. The housing 101 also preferably has a thickness T. Both a top surface 106 and a bottom surface 108, which are oppositely oriented along the housing 101, are defined by the thickness T and the length L, while a left side 111 and a right side 110 of the housing are defined by the width W and the thickness T.

Figure 1F:
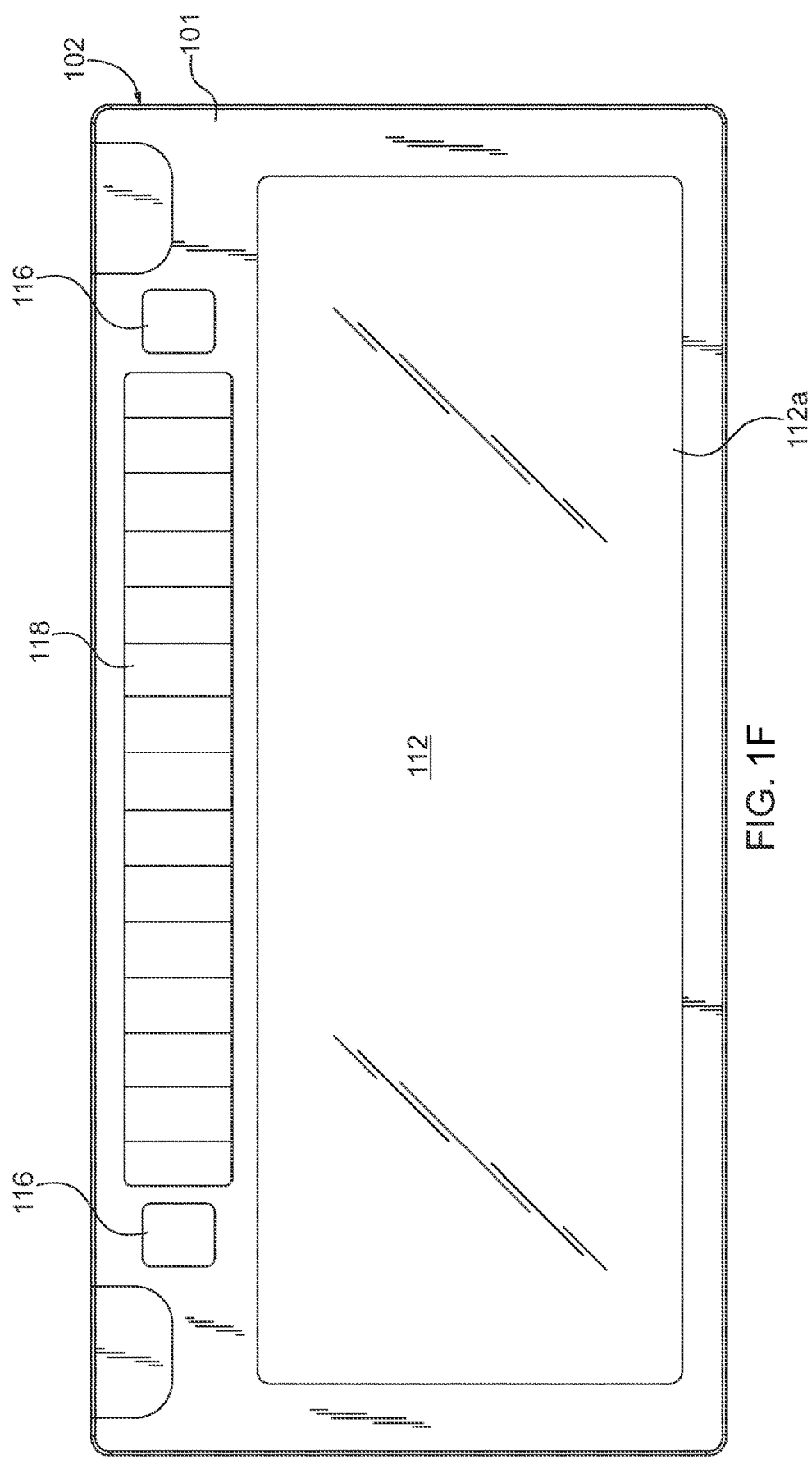
FIG. 1F is a view along a front face of the welding lens of FIG. 1A.
Figure 3:
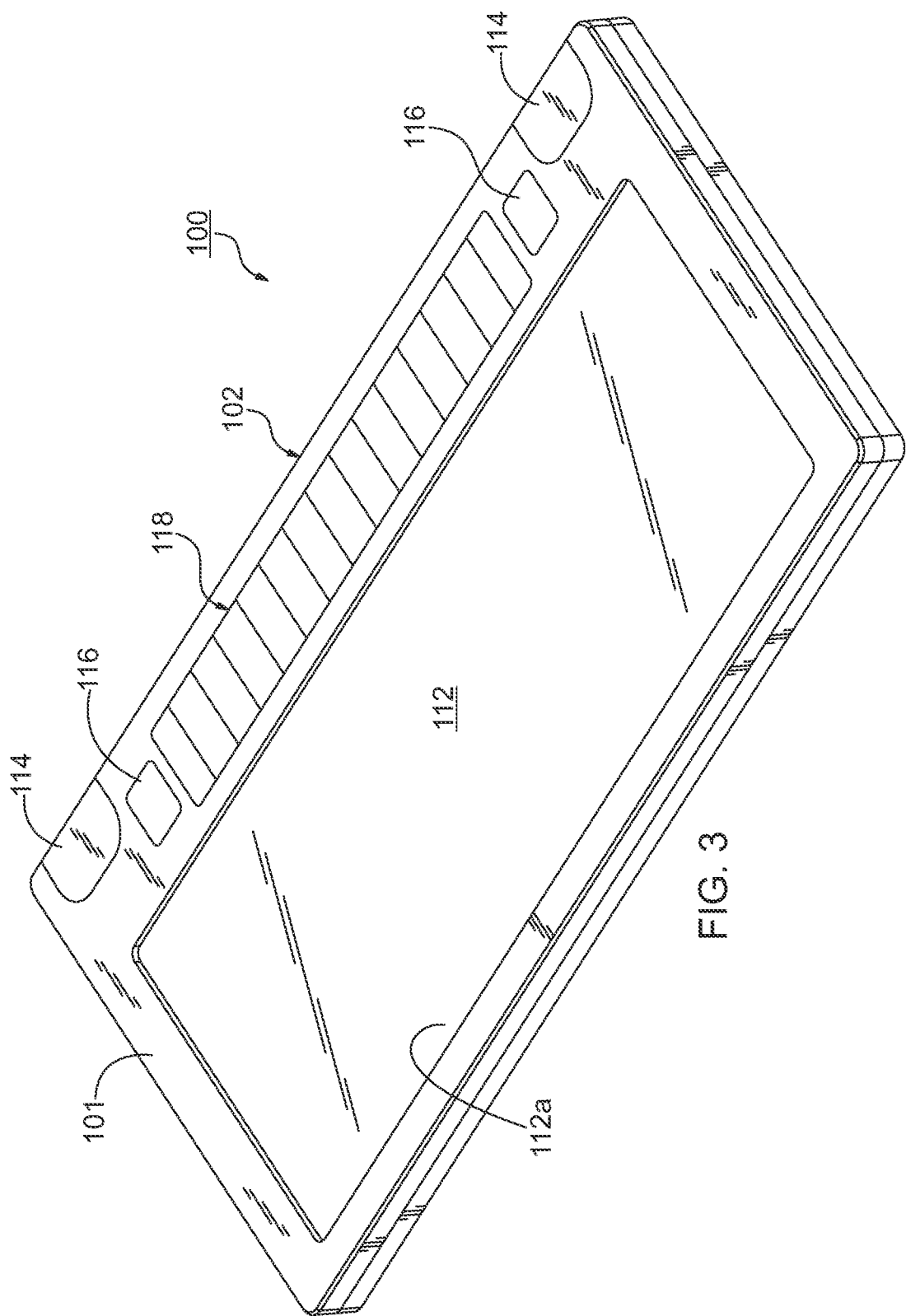
FIG. 3 is a perspective view of the front face shown in FIG. 1F.

The front face 102 of the welding lens 100, shown in FIG. 1F and also in FIG. 3, which faces away from a user in operation, includes a photovoltaic cell 118, or solar cell, a pair of photo-sensors 116, and the front surface 112a of a variable light transmission shutter 112.

Figure 2:
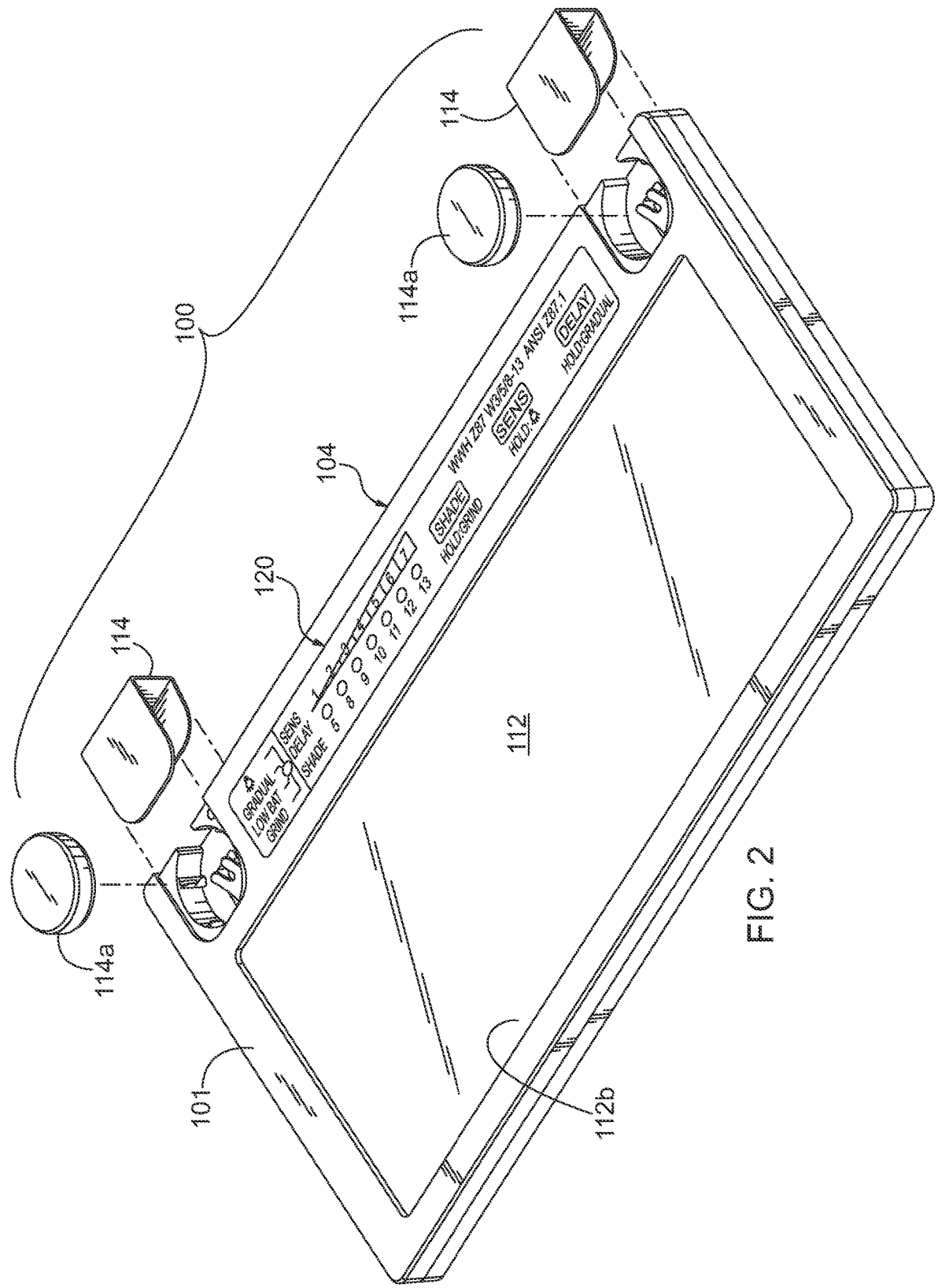
FIG. 2 is a perspective view of the back face shown in FIG. 1A.

The back face 104 of the welding lens 100, shown in FIG. 1A and also in FIG. 2, which faces toward the user in operation, includes a control panel 120 and a back surface 112b of the variable light transmission shutter 112. A pair of removable panels 114 sit along the front face 102, top surface 106, and back face 104. These panels 114 are removable to access batteries 114a, which are likewise removable and insertable as needed to provide at least partial electric power to internal electronic components of the welding lens 100.

The welding lens 100 preferably uses two batteries 114a, with each battery preferably being a lithium 3.0 volt (V) battery, such as a CR927 battery. However other types of batteries, being comparable in size and performance, can be made to work with the welding lens 100. Variations in size and performance of the batteries is acceptable as long as the internal electronic components are properly powered and the batteries fit within the dimensions of the lens housing 101.

The variable light transmission shutter 112 preferably provides a viewing area of 3.8 in.×1.38 in., or 96.52 mm by 35.052 mm.

In the preferred embodiment of the welding lens 100, the width W of the housing 101 is 2 in., or 50.80 mm, the length L of the housing is 4.25 in., or 107.95 mm, and the thickness T of the housing is 0.28 in., or 7.112 mm. These measurements correspond to welding helmets with holders for welding lenses with similar dimensions, such that the welding lenses are removable from the welding helmet and are replaceable with other welding lenses. As previously discussed, at the width W by length L dimensions of 50.80 mm×107.95 mm (2 in.×4.25 in.), welding lens are currently only designed for a single or small range of amperages. Therefore, when currently working between low and high intensity welding processes, such as when welding different types of materials, a user within a helmet having a 50.80 mm×107.95 mm welding lens must remove the welding lens designed for a low intensity and replace it with a welding lens for high intensity, and vice versa. The welding lens 100 of the preferred embodiment is usable for both high intensities and low intensities, and variable intensities in-between. The welding lens 100 therefore provides a new benefit in the art.

The lens housing of prior art welding lenses is made from plastic, which reduces the amount of heat those lens housings can accept before malfunction. The lens housing 101 is preferably made from a metal that reflects infrared radiation, including stainless steel, copper, gold and gold-plated metals, silver, aluminum, and alloys thereof. In the preferred embodiment, the lens housing 101 is made of stainless steel, which reflects infrared radiation emitted from arcs during welding. Infrared radiation causes heat build-up on a welding lens, so reflecting the infrared radiation that contacts the lens housing 101 keeps welding lens 100 cooler and allows for proper operation of an electronic circuit 150 providing multiple shade values within the smaller dimensions described herein.

Figure 4:
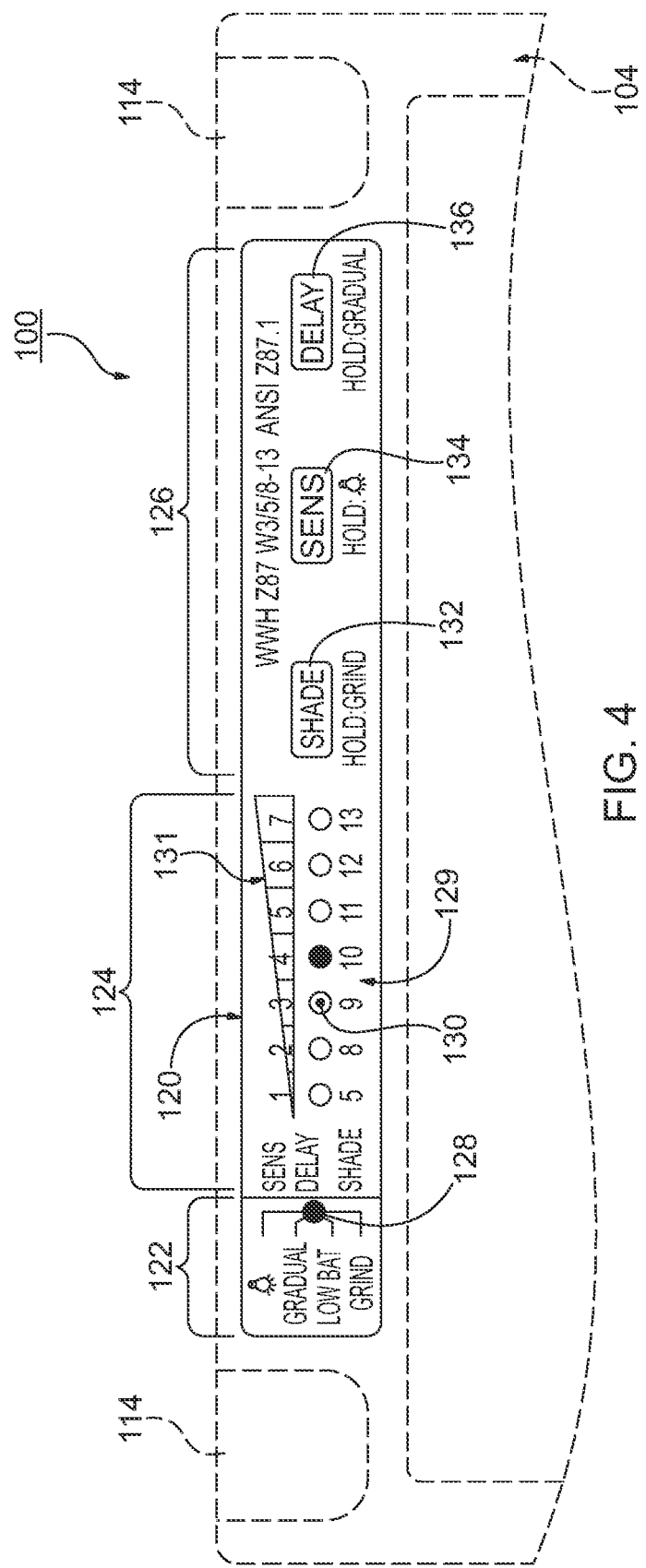
FIG. 4 is a view of a control panel along the back face.

The control panel 120 of the preferred embodiment of the welding lens 100 is shown in greater detail in FIG. 4. The control panel 120 includes a function section 122, an information section 124, and a control section 126. The function section 122 includes an indicator display 128, which in this embodiment is an LED light, namely a red LED light. In other embodiments, the indicator 128 can be a display screen with words, symbols, images, and/or lights. The function section 122, in conjunction with the indicator 128, notifies a user of one or more current functions of the welding lens 100. These functions include an anti-light interference function, a gradual change delay function, a low battery status, or a grind mode status.

When the anti-light interference function is active, the welding lens 100 reduces flickering and sensitivity to ambient light fluctuation from a surrounding environment. Flickering of the variable light transmission shutter 112 is prevented in bright environments and the welding lens 100 adjusts the delay parameters and sensitivity parameters to the ambient light in the surrounding environment.

When the gradual change delay function is active, a change from a dark state of the welding lens 100 to a light state is more gradual. Typically, a normal change from the dark state to the light state is 0.01 seconds (s). When the gradual change delay function is active, the change from the dark state to the light state is 0.5 s. This slower change from the dark state to the light state reduces eye fatigue.

The information section 124 includes a plurality of indicator displays 130 that provide information on sensitivity parameters, delay parameters, and shade parameters. The sensitivity parameters and delay parameters are represented by parameter numbers 1-7, represented in FIG. 4 as 131, with each number corresponding to a respective indicator display 130. The shade parameters are represented by parameter numbers 5 and 8-13, represented in FIG. 4 as 129, with each number 129 corresponding to the respective indicator display 130. Each indicator display 130 of the plurality of indicator displays, in the preferred embodiment of the welding lens 100, is an LED light, namely, a green LED light. Further, the preferred embodiment of the welding lens 100 includes seven indicators 130. In other embodiments, the indicator displays 130 can be a display screen with words, symbols, images, and/or lights. Other embodiments of the welding lens could have more or less than seven different sensitivity parameters, delay parameters, and shade parameters.

The control section 126 includes three buttons 132, 134, and 136. The button 132 corresponds to and allows the user to change active shade parameters, with each shade parameter having a value 5 and 8 through 13 displayed on the control panel 120. The button 134 corresponds to and allows the user to change active sensitivity parameters, with each sensitivity parameter having a value 1 through 7 displayed on the control panel 120. The button 136 corresponds to and allows the user to change active delay parameters, with each delay parameter having a value 1 through 7 displayed on the control panel 120. Each button 132, 134, and 136 has a short press application and a long press application. The delay parameters and sensitivity parameters share parameter numbers 131 on the control panel 120 in the preferred embodiment of the welding lens 100, but may have their own values in other embodiments.

For the shade button 132, the long press application toggles between a welding mode and a grind mode. The user holds down the shade button 132 for 1.5 s or more to toggle between the welding mode and the grind mode. While in the grind mode, the indictor display 128 will flash every 2 s and stay lit for 0.3 s during each flash to indicate that the welding lens 100 is in grind mode. Further, while in grind mode, the plurality of indicators 130 will turn off. While in welding mode, the short press application, whereby the user presses the shade button 132 for 0.1 s and releases it, will toggle between seven shade levels corresponding, in order, to a 5, 8, 9, 10, 11, 12, and 13 DIN value, with an indicator display 130 lighting up to the corresponding shade setting. When the welding lens 100 is in grind mode, the shade parameter is automatically set to 5.

For the sensitivity button 134, the long press application toggles the anti-light interference function on and off. The user holds down the sensitivity button 134 for 1.5 s or more to toggle the anti-light interference function on and off. When the anti-light interference function is turned on, the indicator display 128 will flash. When the anti-light interference function is turned off, the indicator display 128 will turn off. The short press application, which is when the user presses the sensitivity button 134 for 0.1 s and releases it, whether or not the anti-light interference function is on or off, toggles between different sensitivity levels, which are 1, 2, 3, 4, 5, 6, and 7 in order of increasing sensitivity, with sensitivity level 1 being the lowest sensitivity and sensitivity level 7 being the highest sensitivity. The first short press application of the sensitivity button 134 will cause the corresponding indicator display 130 to start flashing to identify the current sensitivity level. Subsequent short press applications of the sensitivity button 134 will toggle between the sensitivity levels in order up to 7, then back to 1, repeating. The sensitivity levels may vary, as well as the sensitivity values for each sensitivity parameter.

For the delay button 136, the long press application, holding the delay button 136 for 1.5 s or more, toggles the gradual change delay function on and off. When the gradual change delay function is turned on, the indicator display 128 will flash. When the gradual change delay function is turned off, the indicator display 128 will turn off. The short press application, which is when the user presses the delay button 136 for 0.1 s and releases it, whether or not gradual change delay function is on or off, toggles between different delay levels, which are 1, 2, 3, 4, 5, 6, and 7 in order of increasing delays between the light state and the dark state. The first short press application of the delay button 136 will cause the corresponding indicator display 130 to start flashing to identify the current delay level. Subsequent short press applications to the delay button 136 will toggle between the delay levels in order up to 7, then back to 1, repeating. The delay levels may vary, as well as the time values for each delay parameter. In the preferred embodiment of the welding lens, delay level 1 corresponds to a 0.06 s delay and delay level 7 corresponds to a 1.00 s delay, with delay levels 2, 3, 4, 5, and 6 corresponding to values there between.

In the preferred embodiment, when any of the buttons 132, 134, or 136 are pressed, the corresponding indicator 130, for the current level value of the corresponding button, will flash every 1.2 s and stay lit for 0.3 s. The flashing of the corresponding indicator 130 will stop after 5 s without any further button 132, 134, or 136 presses. This flashing of the indicator is given a high priority within the electronic circuit 150 of the welding lens.

Returning to the indicator 128, there are three different levels of priority when indicating functions, a high priority, a medium priority, and a low priority. In an event of a conflict between a higher priority function and a lower priority function, the indicator 128 will give priority to display the higher priority function.

The high priority is given to any long press application of the buttons 132, 134, or 136. In that case, when the button 132, 134, or 136 is pressed with a long press application, the indicator display 128 will flash every 1.2 s and stay lit for 0.3 s. The flashing of the indicator display 128 will stop after 5 s without any further presses of button 132, 134, or 136.

The medium priority level for the indicator display 128 is given to a low battery warning. In that case, the indicator will remain on, without flashing, until the battery 114a is replaced.

The low priority level for the indicator display 128 is given to the grinding mode. As discussed, once grinding mode is activated, the indicator display 128 will flash every 2 s and stay lit for 0.3 s at time.

To preserve battery life, an embodiment of the welding lens 100 may include a sleep mode. The welding lens 100 will automatically enter the sleep mode if no arc light has been sensed in 15 minutes and ambient light intensity is less than 10 Lux (lx). In the sleep mode, the variable light transmission shutter 112 will not automatically darken to the selected shade level. The welding lens will continue to operate in the low-power sleep mode until any button 132, 134, or 136 is pressed or if ambient light is greater than 10 lx, at which point the welding lens will revert to a normal mode within 3 s.

Figure 5:
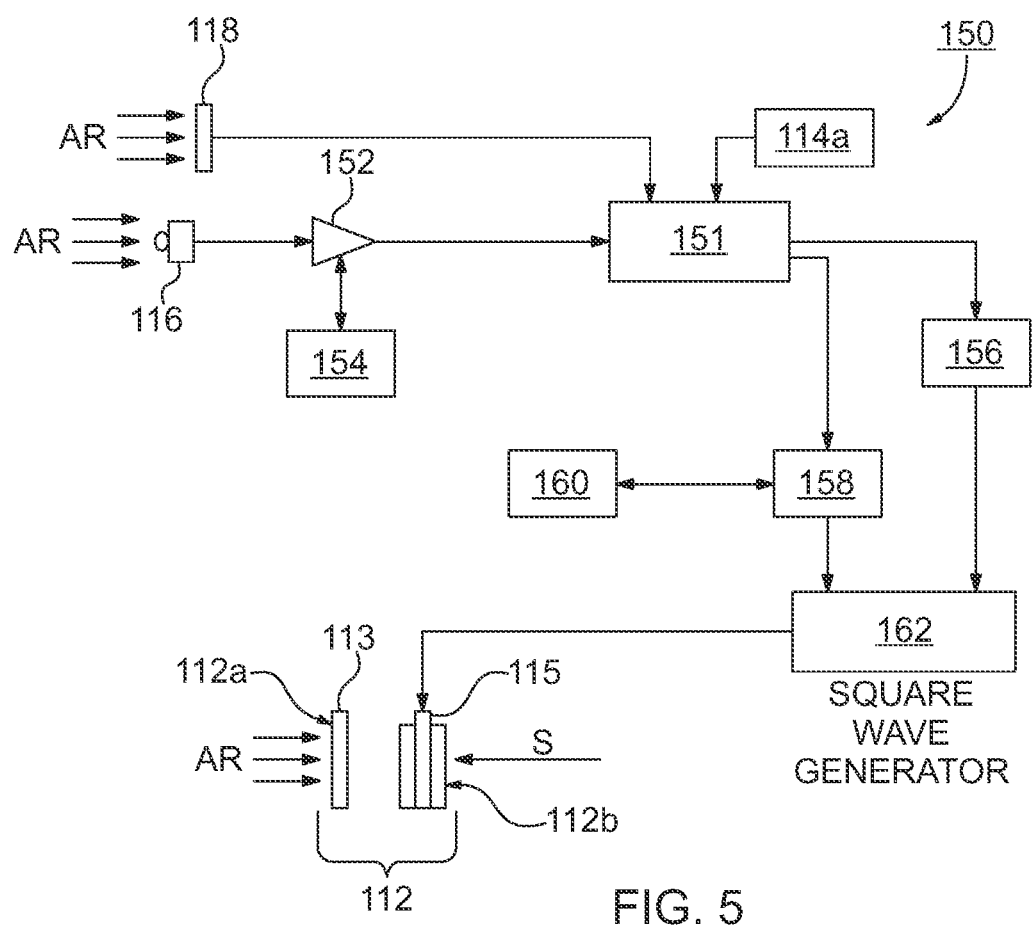
FIG. 5 is an illustration of communication between internal electronic components of the welding lens if FIG. 1A.

FIG. 5 illustrates the electronic circuit 150, which includes the internal electronic components, the control panel 120, the photovoltaic cell 118, the pair of photosensors 116, and the variable light transmission shutter 112. The internal electronic components include a filter and amplifying circuit 152, a delay time and sensitivity control circuit 154, a power control circuit 151, an instantaneous high pulse voltage generator 156, a voltage regulation and control circuit 158, a temperature compensating circuit, and a square-wave generator 162.

When powered on and in the absence of the arc rays AR or other high-intensity light source, the welding lens 100 is in a light state. In the light state, the variable light transmission shutter 112 is at Shade 3. In the presence of the high-intensity light source, such as the arc rays AR, the photo-sensors 116, which can be infrared receivers or other known types of photo-receivers, send an initial signal to the filter and amplifying circuit 152, which sends a signal to the delay time and sensitivity control circuit 154. The circuit 154 sends a signal back to the circuit 152 containing information on the current settings of the delay parameters and the sensitivity parameters. The circuit 152 then sends a signal, containing the current delay parameters and the sensitivity parameters, as well as the current shade parameters, to the power control circuit 151.

Further, as the arc rays AR contacts the photo-sensors 116 to generate the initial signal, any arc rays AR contacting the photovoltaic cell 118 allows the photovoltaic cell to generate electrical power, which is sent to the power control circuit 151. The batteries 114a are also connected to the circuit 151 to provide necessary power when there is insufficient light-derived power generated by the photovoltaic cell 118 supplied to the circuit 151.

The power control circuit 151 then sends a signal to both the voltage regulation and control circuit 158 and the instantaneous high-pulse voltage generator 156. The circuit 158 sends a signal to the temperature compensating circuit 160, which sends a signal back to circuit 158 that may correct an output characteristic of circuit 158 when it is influenced by an operating temperature or temperature characteristics of the internal electronic components. The circuit 158 and circuit 156 then both send a signal to the square wave generator 162. The generator 162 then sends a signal to a liquid crystal light valve 115, which darkens to the dark state based on the shade parameters inputted from the signal sent from the square wave generator 162.

Once the photo-sensors 116 stop receiving arc rays AR, the signal chain described above stops and the variable light transmission shutter 112 reverts to the light state.

The variable light transmission shutter 112 includes at least a coated glass pane 113 along the front face 102 to protect the user against infrared and/or ultraviolet light, and the liquid crystal light valve 115 behind the coated glass pane. A second coated glass pane may be positioned behind the liquid crystal light valve 115 along the back face 104. In such an embodiment, the liquid crystal light valve 115 is sandwiched between the two coated glass panes.

The welding lens 100 is designed for use with GMAW, GTAW, manual metal arc welding (MMAW), or plasma arc cutting or gouging. The auto-darkening feature of the welding lens 100 allows the variable light transmission shutter 112 to automatically change from the light state to the dark state when arc welding starts, and to automatically change from the dark state back to the light state when the arc stops.

The welding lens 100 may be used in manufacturing, including architectural and structural metals, mining, agriculture, motor vehicles, aerospace, shipbuilding, or pipelines; or in construction, including residential, commercial, bridges, dams, or utilities; or any other industry where welders may work.

I claim:

1. A welding lens, comprising:
   a lens housing having a front face and a back face, the front face and back face being oppositely positioned;
   the front face having a photovoltaic cell, at least one photo-sensor, and a variable light transmission shutter; and
   the back face having a control panel and the variable light transmission shutter,
   wherein the lens housing is made of a metal that reflects infrared radiation for the purpose of reducing heat build-up on internal electronic components and has a width of 50.80 millimeters (mm) and a length of 107.95 mm,
   wherein the variable light transmission shutter provides a shade value between 5 and 13 DIN, and
   wherein the variable light transmission shutter automatically darkens to a dark state in response to the at least one photo-sensor receiving a high-intensity light and automatically reverts to a light state when the at least one photo-sensor does not receive the high-intensity light.

2. The welding lens of claim 1, wherein the internal electronic components are in electronic communication with the photovoltaic cell, the at least one photo-sensor, and the variable light transmission shutter.

3. The welding lens of claim 2, wherein the internal electronic components provide an anti-light interference function that reduces flickering in the variable light transmission shutter by reducing sensitivity to ambient light fluctuations.

4. The welding lens of claim 2, wherein the internal electronic components provide a gradual change delay function which delays time taken for the variable light transmission shutter to automatically revert to the light state from the dark state.

5. The welding lens of claim 4, wherein, when the gradual change delay function is active, the variable light transmission shutter takes 0.5 seconds to revert from the light state to the dark state, and, when the gradual change delay function is inactive, the variable light transmission shutter takes 0.1 seconds to revert from the light state to the dark state.

6. The welding lens of claim 2, wherein the internal electronic components provide a grind mode and a welding mode.

7. The welding lens of claim 6, wherein the grind mode provides the shade value of 5 DIN.

8. The welding lens of claim 6, wherein the welding mode provides the shade value of 8-13 DIN.

9. The welding lens of claim 2, further comprising a shade button, a sensitivity button, and a delay button in electronic communication with the internal electronic components.

10. The welding lens of claim 9, wherein the shade button toggles between different shade values of the shade value and toggles between a grind mode and a welding mode, the grind mode providing the shade value of 5 DIN and the welding mode providing the shade value between 8-13 DIN.

11. The welding lens of claim 9, wherein the sensitivity button toggles between different sensitivity values and activates and deactivates an anti-light interference function that reduces flickering in the variable light transmission shutter by reducing sensitivity to ambient light fluctuations.

12. The welding lens of claim 9, wherein the delay button toggles between different delay values and activates and deactivates a gradual change delay function, which, when active, the variable light transmission shutter takes 0.5 seconds to revert from the light state to the dark state, and, when the gradual change delay function is inactive, the variable light transmission shutter takes 0.1 seconds to revert from the light state to the dark state.

13. The welding lens of claim 1, further comprising at least one battery.

14. The welding lens of claim 13, wherein the photovoltaic cell and the battery both provide electric power to internal electronic components of the welding lens.

15. The welding lens of claim 1, wherein the lens housing has a thickness of 7.112 mm.

16. The welding lens of claim 1, wherein the lens frame includes two removable panels, each panel of the two removable panels housing a battery of the at least one battery between each said panel and the lens frame.

17. The welding lens of claim 1, further comprising a control panel having a display indicating a sensitivity value, a shade value, and a delay value.

18. The welding lens of claim 17, wherein the control panel further comprises a sensitivity button to change the sensitivity value, a shade button to change the shade value, and a delay button to change the delay value.

19. The welding lens of claim 1, wherein the metal that reflects the infrared radiation is stainless steel, copper, gold, silver, aluminum, or alloys thereof.

* * * * *